United States Patent
Cottrell et al.

(10) Patent No.: US 6,588,374 B1
(45) Date of Patent: Jul. 8, 2003

(54) HIGH CONCENTRATION TOPICAL INSECTICIDE

(75) Inventors: Ian William Cottrell, Basking Ridge, NJ (US); Michael William Lytwyn, East Hanover, NJ (US); Christine Marie Monro, Oakland, NJ (US); Albert Ahn, Short Hills, NJ (US); Pierre Rosemond Joseph, Hamilton, NJ (US)

(73) Assignee: The Hartz Mountain Corporation, Secaucus, NJ (US)

( * ) Notice: Subject to any disclaimer, the term of this patent is extended or adjusted under 35 U.S.C. 154(b) by 0 days.

(21) Appl. No.: 10/242,550

(22) Filed: Sep. 12, 2002

(51) Int. Cl.⁷ .................. A01K 29/00; A01N 25/00; A01N 25/32
(52) U.S. Cl. .................. 119/651; 424/403; 424/405
(58) Field of Search .................. 119/651, 652, 119/656, 660, 670, 673, 677; 424/401, 402, 403, 404, 405, 406; 514/471

(56) References Cited

U.S. PATENT DOCUMENTS

| 5,434,181 A | 7/1995 | Kodaka et al. |
| 5,532,365 A | 7/1996 | Kodaka et al. |
| 6,274,570 B1 * | 8/2001 | Vogt et al. .................. 514/89 |
| 6,479,542 B2 | 11/2002 | Sembo et al. |

FOREIGN PATENT DOCUMENTS

| JP | 3-220176 | * | 9/1991 |
| WO | WO 02/05639 A2 | * | 1/2002 |

* cited by examiner

*Primary Examiner*—Yvonne Abbott
(74) *Attorney, Agent, or Firm*—Stroock & Stroock & Lavan LLP

(57) ABSTRACT

A topical insecticide is provided which can be safe to use and avoids many common deleterious side effects of conventional topical insecticides. In one preferred embodiment of the invention, the active ingredient of the insecticide formulation is an amine derivative, having a nitro-methylene group, a nitroamino group or a cyanoamino group, which can be formulated to have low toxicity and excellent insecticidal activity. One particularly suitable insecticide is 1-{(tetrahydro-3-furanyl)methyl}-2-nitro-3-methylguanidine (dinotefuran), an aldulticide that will kill adult fleas, dissolved in phenyl methanol or ethanol and ethyl lactate.

19 Claims, No Drawings

HIGH CONCENTRATION TOPICAL INSECTICIDE

BACKGROUND OF INVENTION

The invention relates generally to insecticides and more particularly to a topical insecticide, such as one suitable to use on house pets such as cats and dogs.

The infestation of animals with fleas, ticks, flies and the like is highly undesirable. Accordingly, it has become common to administer both topical and internal insecticides to livestock and pets. Topical applications can be desirable, in that many insecticides are acceptably safe when used topically, but not when used internally.

Various topical insecticides have drawbacks. Some require a large volume to be applied to the animal. This can cause considerable mess and can lead to an unpleasant smell. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

Accordingly, it is desirable to provide an improved topical insecticide, which overcomes drawbacks of the prior art.

SUMMARY OF THE INVENTION

Generally speaking, in accordance with the invention, a topical insecticide is provided which can be safe to use and avoids many common deleterious side effects of conventional topical insecticides. In one preferred embodiment of the invention, the active ingredient of the insecticide formulation is an amine derivative, having a nitro-methylene group, a nitroamino group or a cyanoamino group, which can be formulated to have low toxicity and excellent insecticidal activity. Active ingredients of insecticides and their method of formation in accordance with the preferred embodiments of the invention are discussed in U.S. Pat. Nos. 5,532,365 and 5,434,181, the contents of which are incorporated herein by reference. One particularly suitable insecticide is 1-{(tetrahydro-3-furanyl)methyl}-2-nitro-3-methylguanidine (dinotefuran). Dinotefuran is an aldulticide that will kill adult fleas.

In one preferred embodiment of the invention, the active portion of the insecticide formulation comprises (tetrahydro-3-furanyl)methylamine derivatives of following formula (1).

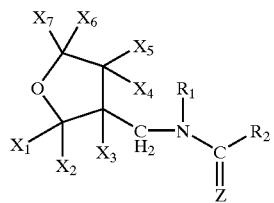

Active ingredients and insecticides in accordance with preferred embodiments of the invention are generally available as crystals and solids. Therefore, they need to be dissolved or otherwise put into a liquid form for use as topical spot products on animals. Topical spot products are more advantageous if the amount of liquid applied can be minimized. This must be balanced with the need for appropriate dosage to achieve the desired insecticidal effect. Therefore, it is desirable to use a solvent that will allow the solubilization of a high concentration of insecticide.

It has been determined that the insecticidal materials of the invention are advantageously dissolved in alcohols, but to relatively low concentrations. Phenyl methanol, is an alcohol, also known as benzyl alcohol, and is a liquid, somewhat soluble in water. It is routinely used in perfumes, flavors, photographi-c developers, dyes, films and inks and has other uses. It was surprisingly discovered that a relatively high concentration of the insecticide can be solubilized in phenyl methanol.

In one aspect of the current invention, the compound is dissolved in solvent to a concentration range of 2–20%, more preferably 4–17% and most preferably about 8 to 14%, with 12.5% as a preferred example. All percentages, unless otherwise evident, are on a weight basis.

In another preferred embodiment of the invention, the preferred solvent component comprises a mixture comprising water, ethyl lactate and ethanol, wherein the final concentration of ethyl lactate ranges from 5–20% and the final concentration of ethanol ranges from 30–45%, more preferably 7–15% ethyl lactate and 35–43% ethanol and most preferable a final concentration of 10% ethyl lactate and 40% ethanol. The remainder can be water. Isopropanol can also be added to ethanol to improve solubility.

Accordingly, it is an object of the invention to provide an improved topical insecticide, which overcomes drawbacks of the prior art.

DETAILED DESCRIPTION OF THE PREFERRED EMBODIMENTS

The novel (tetrahydro-3-furanyl)methylamine derivatives of the formula (1) have an excellent insecticidal activity even in the absence of a pyridylmethyl group or a thiazolylmethyl group in their molecular structure. According to the present invention, there are provided (tetrahydro-3-furanyl) methylamine derivatives represented by formula (1), where $X_1$, $X_2$, $X_3$, $X_4$, $X_5$, $X_6$ and $X_7$ represent each a hydrogen atom or an alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or —N($Y_1$)$Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl)

methyl group or a benzyl group, and $Y_2$ represents a hydrogen atom or an alkyl group having from 1 to 5 carbon atoms); and Z represents =N—NO$_2$, =CH—NO$_2$ or =N—CN; insecticides containing the derivatives as an effective ingredient; and intermediates for producing the compounds of the formula (1) represented by a formula (2):

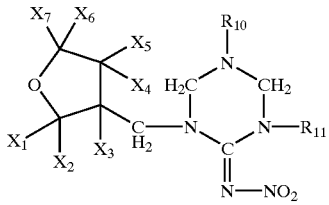

where $X_1$, $X_2$, $X_3$, $X_4$, $X_5$, $X_6$ and $X_7$ represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

The novel (tetrahydro-3-furanyl)methylamine derivatives of the formula (1) and formula (2) according to the invention are excellent compounds having a high insecticidal power and broad insecticidal spectrum. Further, agricultural chemicals containing the novel (tetrahydro-3-furanyl) methylamine derivatives of the formula (1) and (2) according to the invention have outstanding characteristics as insecticides and hence are useful.

Specific examples of the alkyl group for $X_1$, $X_2$, $X_3$, $X_4$, $X_5$, $X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for $R_1$ include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for $R_1$ include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropyl-carbonyl group.

Specific examples of the alkylamino group for $R_2$ include a methylamino group, an ethylamino group, an n-propylamino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butyl-carbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methyl-vinylcarbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclo-hexylcarbonyl group, and the like, preferably a cyclopropyl-carbonyl group.

Specific examples of the benzoyl group substituted byalkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

In the development of a formulation for use on animals, there are several parameters that must be considered. These are:

(a) Concentration high enough to minimize the volume of the topical applied to the animal (one would not want to put 20 ml, e.g., onto a small cat).

(b) The formulation should be stable for one month at 130° F., 100° F., 40° F., room temperature and 0° F. This helps ensure that the formulation remains stable under the conditions that it could meet in commerce.

(c) Safe to use on the animal—particularly non-irritating since the product is applied to the skin. Also safe if ingested by the animal; ingestion can occur when cats groom themselves.

(d) Safe to use by the consumer.

(e) Efficacious in use—should kill greater than 90% of the fleas up to 28 days.

(f) Efficacy would be reduced if crystallization occurred in the package.

(g) Needs to be aesthetically pleasing—"no oily drop" on the animal when applied.

(h) Fast drying to reduce the chance of the animal shaking off the liquid thereby reducing efficacy.

(i) Microbiologically stable.

The above-referenced patents recognize different possible solvents, but do not provide information on how to formulate insecticide in a non-irritating manner. No examples were given in which the compounds were used on animals. Additionally, in all of the examples given the compounds were dissolved into solvents that are undesirable to use on animals. Specifically, acetone, used in all but one of the examples, is very irritating by both inhalation and skin contact, due to de-fatting action on skin and mucous membranes. It is also very irritating to the eyes. Accordingly, there is a need to develop a different solvent for these compounds that can be used on animals. The present formulation satisfies the parameters detailed above.

It has been found that when the solvent comprises phenyl methanol or a combination of ethyl lactate and ethanol, higher concentrations of active ingredient can be incorporated. In one aspect of the current invention, the active compound is dissolved in solvent to a concentration range of 2–20%, more preferably 4–17% and most preferably about 8 to 14%, with 12.5% as a preferred example. All percentages, unless otherwise evident, are on a weight basis.

In another preferred embodiment of the invention, the preferred solvent component comprises a mixture comprising water, ethyl lactate and ethanol, wherein the final concentration of ethyl lactate ranges from 5–20% and the final concentration of ethanol ranges from 30–45%, more preferably 7–15% ethyl lactate and 35–43% ethanol and most preferable a final concentration of 10% ethyl lactate and 40% ethanol. The remainder can be water. Isopropanol can also be added to ethanol to improve solubility.

In one embodiment of the invention, the preferred solvent component comprises a mixture comprising water and ethanol at a concentration range of 50–80% ethanol, more preferably 65–75% ethanol and most preferably about 69–71% ethanol, with a preferred example 70% ethanol. The remainder can be water. The insecticide formulation can include various additions to the ethanol/water combination.

In another embodiment of the invention, the preferred solvent component comprises a mixture comprising water, ethanol and isopropanol, wherein the final concentration of total alcohol range from 50–80% alcohol, more preferably 65–75% alcohol and most preferably about 69–71% alcohol, with a preferred example 70% alcohol. The remainder can be water. The concentration of ethanol and isopropanol are 25–45% ethanol, 25–45% isopropanol, more preferably 30–40% ethanol, 30–40% isopropanol and most preferably 35% ethanol and 35% isopropanol.

In another embodiment of the invention, the solvent comprises a mixture comprising dipropyleneglycol monomethyl ether (DPM) and water at a concentration range of about 30–70% DPM, more preferably about 45–55% DPM and most preferably about 50% DPM/50% water mixture.

In yet another embodiment of the invention, the preferred solvent is a mixture comprising water, ethanol and DPM at a concentration range of 25–40% ethanol, 25–40% DPM, more preferably 30–35% ethanol, 30–35% DPM and most preferably equal volumes of each component (i.e., 33% ethanol, 33% DPM and 33% water).

The following examples are given for purposes of illustration only and are not intended to be construed in a limiting manner.

EXAMPLE 1

Preparation of 1-{(Tetrahydro-3-furanyl)methyl}-2-nitro-3-methylguanidine(dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroiminohexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: ethyl acetate/hexane=1/1) to obtain 7.8 g of 1-{(tetrahydro-3-furanyl) methyl}-2-nitro-3-methylguanidine (dinotefuran).

EXAMPLE 2

Preparation of Insecticide Formulation Containing Dinetofuran, Ethanol and Water 5 g (i.e., 5.6% (weight/weight)) of dinotefuran was dissolved into 100 ml of a mixture comprising 70% ethanol and 30% water. The resulting mixture can be spot applied to companion animals, such as dogs and cats and will kill fleas, ticks and other insects.

EXAMPLE 3

Preparation of Insecticide Formulation Containing Dinetofuran and Phenyl Methanol 15 g (i.e., 12.5% (weight/weight)) of dinotefuran was dissolved into 100 ml of phenyl methanol. The resulting solution can be spot applied to companion animals, such as dogs and cats and will kill fleas, ticks and other insects.

EXAMPLE 4

In Vivo Activity of a Flea Dermal Treatment Against the Cat Flea (*Ctenocephalides felis*) on Cats Eighteen cats were separated into three groups each containing 6 cats. Group 1 (6 cats each weighing 9 lbs. or less) remained untreated as Non-Treated Controls. Group 2 (6 cats each over 9 lbs.) were treated with 3.4 ml of the dinotefuran insecticide formulation (5.71% w/w). Group 3 (6 cats each weighing 9 lbs. or less) were treated with 1.5 ml of the dinotefuran insecticide formulation (5.71% w/w).

Approximately 18 hours prior to treatment the cats were infested with 100 cat fleas (*Ctenocephalides felis*), which were applied to the animal's back. Cats in Groups 2 and 3 were then treated with the indicated volume of insecticide by dispensing the liquid at skin level between the shoulder blades. Flea counts were taken at day 1 (i.e., 24 hours post-treatment), day 8, day 15, day 22 and day 29. Cats were re-infested with 100 fleas on days 7, 14, 21, and 28. To determine the efficacy of the dermal treatment, the number of fleas found on treated cats was compared to the number of fleas found on untreated cats. Percent reduction was determined as follows and the results are summarized in Table 1:

Mean Number of fleas on Untreated Cats−Mean Number of fleas on Treated Cats/Mean Number of fleas on Untreated Cats× 100%

As shown in Table 1 the results demonstrate that the dosages used on Groups 2 and 3 are both effective at reducing the number of adult fleas on cats through at least 29 days and thus are effective as a one month dermal treatment.

TABLE 1

| Controlled Percent Reduction in Flea Population | | | | |
|---|---|---|---|---|
| Day 1 | Day 8 | Day 15 | Day 22 | Day 29 |

| | Day 1 | Day 8 | Day 15 | Day 22 | Day 29 |
|---|---|---|---|---|---|
| Control Group 1 | 0 | 0 | 0 | 0 | 0 |
| Group 2 | 100 | 100 | 99 | 99 | 96 |
| Group 3 | 100 | 98 | 95 | 95 | 91 |

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. An insecticide formulated by dissolving an insecticidably effective amount of an insecticidal (tetrahydro-3-furanyl)methylamine derivative in an effective amount of a solvent component comprising water and phenyl methanol or a combination of ethanol and ethyl lactate to dissolve said insecticidably effective amount.

2. The insecticide of claim 1, wherein said insecticidal derivative is dinotefuran.

3. The insecticide of claim 2, wherein the formulation is not irritating to dogs or cats and is effective to kill fleas with applications of less than 20 ml to a cat.

4. The insecticide of claim 2, wherein said solvent component comprises phenyl methanol.

5. The insecticide of claim 4, wherein the formulation is not irritating to dogs or cats and is effective to kill fleas with applications of less than 20 ml to a cat.

6. The insecticide of claim 4, wherein said insecticidal derivative is dissolved in the formulation to a concentration of about 8 to 20%.

7. The insecticide of claim 6, wherein the concentration of ethyl lactate is about 5 to 20% and the concentration of ethanol is about 30–45%.

8. The insecticide of claim 2, wherein said solvent component comprises ethanol and ethyl lactate.

9. The insecticide of claim 8, wherein said insecticidal derivative is dissolved in the formulation to a concentration of about 8 to 20%.

10. The insecticide of claim 8, wherein the concentration of ethyl lactate is about 5 to 20% and the concentration of ethanol is about 30–45%.

11. The insecticide of claim 8, wherein the concentration of ethyl lactate is about 7 to 15% and the concentration of ethanol is about 30–45%.

12. The insecticide of claim 8, wherein the formulation is not irritating to dogs or cats and is effective to kill fleas with applications of less than 20 ml to a cat.

13. The insecticide of claim 1, wherein said insecticidal derivative is dissolved in the formulation to a concentration of about 8 to 20%.

14. The insecticide of claim 13, wherein the concentration of ethyl lactate is about 5 to 20% and the concentration of ethanol is about 30–45%.

15. The insecticide of claim 1, wherein said insecticidal derivative is dissolved in the fomulation to a concentration of about 8 to 14%.

16. The insecticide of claim 1, wherein the formulation is not irritating to dogs or cats and is effective to kill fleas with applications of less than 20 ml to a cat.

17. A method of controlling insect infestation in animals, comprising dissolving dinotefuran in a solvent mixture comprising water and phenyl methanol or ethyl lactate and ethanol and applying an insecticidably effective amount of the solution to an animal.

18. The method of claim 17, wherein the animal is a cat or a dog.

19. The method of claim 18, wherein the insect is a flea.

* * * * *